United States Patent [19]
Satomi et al.

[11] Patent Number: 5,513,639
[45] Date of Patent: May 7, 1996

[54] BALLOON TYPE ULTRASONIC DIAGNOSTIC PROBE

[75] Inventors: Gengi Satomi, #A-23, 3100, Toyoshina Toyoshina-machi, Minamiazumi-gun, Nagano 399-82; Narutaka Nakao, Kawasaki, both of Japan

[73] Assignees: Fujitsu Limited, Kawasaki; Gengi Satomi, Minamiazumi, both of Japan

[21] Appl. No.: 318,162

[22] Filed: Oct. 5, 1994

[30] Foreign Application Priority Data

Apr. 12, 1994 [JP] Japan .................................. 6-073104

[51] Int. Cl.$^6$ ...................................................... A61B 8/12
[52] U.S. Cl. ............................ 128/660.100; 128/662.060
[58] Field of Search ..................... 128/660.100, 662.060, 128/662.030, 662.040, 661.100

[56] References Cited

U.S. PATENT DOCUMENTS

| | | | |
|---|---|---|---|
| 4,466,443 | 8/1984 | Utsugi | 128/660.100 |
| 4,841,979 | 6/1989 | Dow et al. | 128/660.100 |
| 4,860,758 | 8/1989 | Yanagawa et al. | 128/660.100 X |
| 4,930,515 | 6/1990 | Terwilliger | 128/662.060 |
| 4,967,752 | 11/1990 | Blumenthal et al. | 128/660.100 |
| 5,135,001 | 8/1992 | Sinofsky et al. | 128/662.060 |
| 5,215,092 | 6/1993 | Wray | 128/662.060 X |
| 5,305,755 | 4/1994 | Nakao | 128/662.060 X |
| 5,320,104 | 6/1994 | Fearnside et al. | 128/662.060 X |
| 5,331,997 | 7/1994 | Shturmon | 128/662.060 X |
| 5,402,793 | 4/1995 | Gruner et al. | 128/662.060 |

Primary Examiner—Francis Jaworski
Attorney, Agent, or Firm—Staas & Halsey

[57] ABSTRACT

An ultrasonic diagnostic probe comprising an inflatable balloon member attached to the free end of a tubular support member. An array of elongated piezoelectric elements is arranged in the balloon member. Space ensuring side walls are arranged in the balloon member between the balloon member and the array of piezoelectric elements for ensuring a space in which the array of piezoelectric elements can rotate irrespective of the shape balloon member. The balloon member can be inflated by introducing liquid therein. The balloon member is in a deflated condition when the probe is inserted in the esophagus, and can be inflated after the probe is inserted in the esophagus to allow the array of piezoelectric elements to be rotated. The space ensuring side walls are correspondingly deformed.

11 Claims, 7 Drawing Sheets

BALLOON TYPE ULTRASONIC DIAGNOSTIC PROBE

BACKGROUND OF THE INVENTION

1. Field of the Invention

The present invention relates to a balloon type ultrasonic diagnostic probe used for medical purposes.

2. Description of the Related Art

For the medical diagnosis of a patient, an ultrasonic diagnostic probe, having an ultrasonic sensor therein, has been developed. The ultrasonic diagnostic probe is used on the surface of the body, and also in body cavities, to carry out ultrasonic scanning. Ultrasonic scanning in the body cavity provides doctors with more precise data. In the ultrasonic scanning in the body cavity, however, the patient may feel pain during the insertion of the ultrasonic diagnosis probe into the esophagus, and it is required that ultrasonic diagnostic probes have smaller diameters.

Examples of prior art ultrasonic diagnostic probes as shown in FIGS. 7 to 10 of the attached drawings, are used to produce trans-esophageal echo cardiographs. In FIG. 7, the ultrasonic diagnosis probe 1 comprises an array 3 of elongated piezoelectric elements at the free end of the probe 1. Each of the piezoelectric elements is an elongated strip and the array 3 has a rectangular shape with long sides and short sides. The array of piezoelectric elements is arranged in the free end of the probe 1 so that the ultrasonic scanning direction is perpendicular to the longitudinal axis of the ultrasonic diagnostic probe 1. The length of the array 3 in the scanning direction is made small to mitigate the pain inflicted on the patient during the insertion of the ultrasonic diagnosis probe 1 into the body.

In this design, however, an aperture of the sensor becomes smaller if the length of the array 3 elements in the scanning direction is made smaller, and this reduces the quality of obtained images. In addition, since the scanning direction is fixedly determined, only a restricted picture can be obtained.

In FIG. 8, the probe 1 has an array of piezoelectric elements 3 the scanning direction of which coincides with the longitudinal direction of the probe 1. This probe can overcome the problem of the diameter of the sensor, but still suffers from the problem of its small degree of freedom in obtaining a picture.

To solve these problems, a bi-planar-type probe 1 having two arrays 3 of piezoelectric elements having the scanning directions perpendicular to each other is shown in FIG. 9. Also, a multi-planar-type probe 1 having a rotatable array 3 of piezoelectric elements has been proposed, as shown in FIG. 10. However, since the former includes the array 3 of the piezoelectric elements having the scanning direction parallel to the longitudinal direction of the probe 1, and since the latter needs space for the array 3 to piezoelectric elements rotate, these probes also suffer from the problem that the free end of the probe 1 must have a large size. Therefore, these designs inflict great pain on the patient.

SUMMARY OF THE INVENTION

The object of the present invention is to provide an ultrasonic diagnostic probe by which the pain inflicted on the patient during the insertion of the probe into a body cavity can be mitigated and an image of a good quality can be obtained.

According to one aspect of the present invention, there is provided an ultrasonic diagnostic probe comprising a tubular support member having a free end and an axis; an inflatable balloon member attached to the free end of the tubular support member; an array of elongated piezoelectric elements arranged in the balloon member, the array of piezoelectric elements being arranged in a generally rectangular shape with long sides and short sides and rotatable about an axis of rotation; and space ensuring means, including a wall means, arranged in the balloon member between the balloon member and the array of piezoelectric elements for ensuring a space in which the array of piezoelectric elements can rotate irrespective of the shape of the balloon member, so that the angle of the long sides of the array of piezoelectric elements relative to the axis of the tubular support member at the free end thereof can be changed.

According to another aspect of the present invention, there is provided an ultrasonic diagnostic probe comprising a tubular support member having a free end and an axis; an inflatable balloon member arranged on the free end of the tubular support member; an array of elongated piezoelectric elements arranged in the balloon member, the array of piezoelectric elements having a generally rectangular shape with long sides and short sides and rotatable about an axis of rotation; and a tube arranged in the tubular support member for introducing fluid into the balloon member to inflate the latter, whereby the angle of the long sides of the array of piezoelectric elements relative to the axis of the tubular support member at the free end thereof can be changed.

BRIEF DESCRIPTION OF THE DRAWINGS

The present invention will become more apparent from the following description of the preferred embodiments, with reference to the accompanying drawings, in which.

DESCRIPTION OF THE PREFERRED EMBODIMENTS

Figure 1:
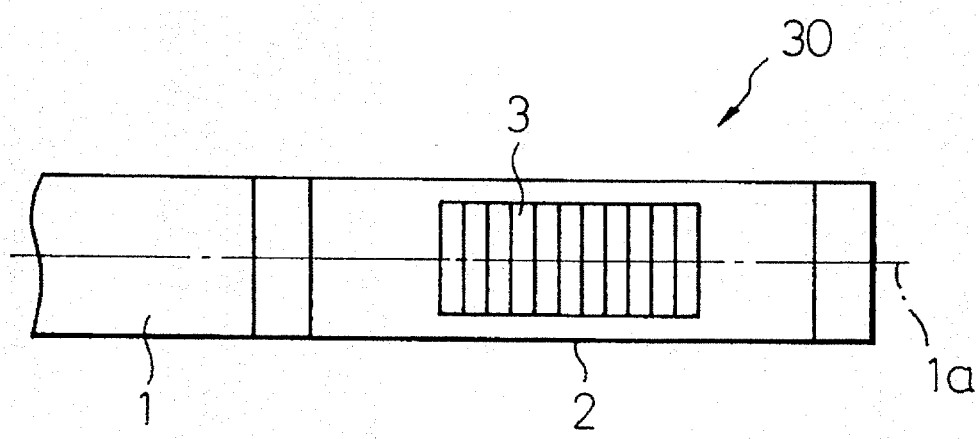
FIG. 1 is a diagrammatic view of an ultrasonic diagnosis probe according to the first embodiment of the present invention.
Figure 2:
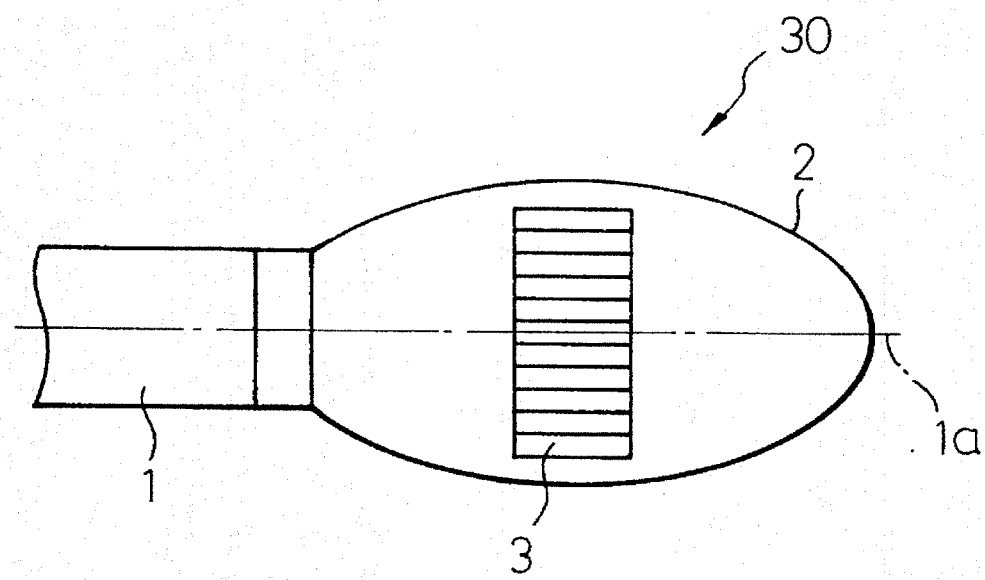
FIG. 2 is a diagrammatic plan of the ultrasonic diagnosis of FIG. 1 in another condition.

FIGS. 1 and 2 show, in principle, an ultrasonic diagnosis probe according to the present invention. The ultrasonic diagnosis probe 30 comprises a tubular support member or tubular shaft 1 having a free end and an axis 1a, and an inflatable balloon member 2 attached to the free end of the tubular support member 1. An array 3 of elongated piezoelectric elements is rotatably arranged in the balloon member 2. The array 3 of piezoelectric elements has the generally rectangular shape of a block, and thus has long sides and short sides. Space ensuring wall means (not shown in FIGS. 1 and 2) can be arranged in the balloon member 2 for ensuring a space in which the array 3 of piezoelectric elements can rotate. Also, a tube (not shown in FIGS. 1 and 2) can be arranged in the tubular support member 1 for introducing fluid such as water into the balloon member 2 to inflate the latter.

In FIG. 1, when the ultrasonic diagnostic probe 30 is inserted in a body cavity such as the esophagus, the array 3 of piezoelectric elements is brought in such a position that the long sides of the array 3 of piezoelectric elements are generally parallel to the axis 1a of the tubular support member 1 at the free end thereof. In addition, the balloon member 2 is deflated. Therefore, the pain inflicted on the patient during the insertion of the ultrasonic diagnosis probe 30 can be mitigated.

After the ultrasonic diagnosis probe 30 is inserted in the body cavity, the balloon member 2 is inflated, depending on the disposition of the array 3 of piezoelectric elements and the array 3 of piezoelectric elements is rotated so that the long sides thereof are generally perpendicular to the axis 1a of the tubular support member 1 at the free end thereof. Once the ultrasonic diagnosis probe 30 is inserted in the body cavity and while the diagnosis is carried out, the patient does not feel pain even if the size of the end portion of the ultrasonic diagnosis probe 30 is enlarged. The array 3 of piezoelectric elements can take any intermediate positions between the positions of FIGS. 1 and 2. Therefore, an image of a good quality can be obtained by using the ultrasonic diagnostic probe 30.

FIGS. 3 to 6 show in greater detail an ultrasonic diagnosis probe according to the present invention. The ultrasonic diagnosis probe 30 is used to produce trans-esophageal echo cardiographs. The ultrasonic diagnosis probe 30 comprises a tubular support member 1 having a free end and an axis 1a, a cap member 5 fixed to the end of the tubular support member 1, an array 3 of piezoelectric elements rotatably supported by the cap member 5, a space ensuring means 4 for ensuring a space in which the array 3 of piezoelectric elements can rotate, and an inflatable balloon member 2 attached to the free end region of the tubular support member 1 and surrounding the array 3 of piezoelectric elements.

The cap member 5 comprises a head 5a at the distal end of the cap member 5, away from the tubular support member 1, a body 5b extending between the free end of the tubular support member 1 and the head 5a, and a pin guide wall 5c arranged at the rear end of the support body 5b. The rear end of the body 5b with the pin guide wall 5c is fixed to the free end of the tubular support member 1. The ultrasonic diagnosis probe 30 is formed in a generally uniform cylindrical shape as a whole, and to this end, the head 5a has a diameter identical to that of the tubular support member 1. Also, the body 5b and the pin guide wall 5c are designed in such a shape that they are accommodated in a cylinderical generatrix formed by the outer circumferential surface of the head 5a.

The array 3 of piezoelectric elements comprises a plurality of elongated strip-shaped piezoelectric elements 3b such as piezoelectric ceramics arranged in a row, and has a generally rectangular shape with long sides and short sides. The array 3 of piezoelectric elements has an ultrasonic transmitting and receiving surface 3a (FIG. 4) and a packing material (not shown) or the like is applied to the opposite surface of the array 3.

The length of the short sides of the array 3 of piezoelectric elements is made as small as possible, and preferably, approximately identical to or slightly smaller than the inside diameter of the tubular support member 1. At this size, the ultrasonic diagnosis probe 30 can be designed to have an end portion of a smaller diameter when the scanning direction thereof is perpendicular to the axis 1a of the tubular support member and the long sides of the array 3 of piezoelectric elements is parallel to the axis 1a of the tubular support member 1. Therefore, the ultrasonic diagnosis probe 30 can be smoothly inserted into the esophagus and the pain inflicted on the patient during the insertion of the ultrasonic diagnosis probe 30 can be mitigated.

The array 3 of piezoelectric elements is fixed to a rotor 9. The rotor 9 comprises a disk 9a to which the array 3 of piezoelectric elements is fixed, and a shaft 9b standing at the center of the lower surface of the disk 9a. The shaft 9b is slidably inserted in a hole in the body 5b of the cap member 5. The shaft 9b has a through hole (not shown) through which a cable 3c extends from the array 3 of piezoelectric elements.

The shaft 9b has a pulley 10 fixed thereto. A wire 11 is wound on the pulley 10 for operation by manipulation device (not shown), so that the rotor 9 and the array 3 of piezoelectric elements are rotated by operating the wire 11.

Figure 5:
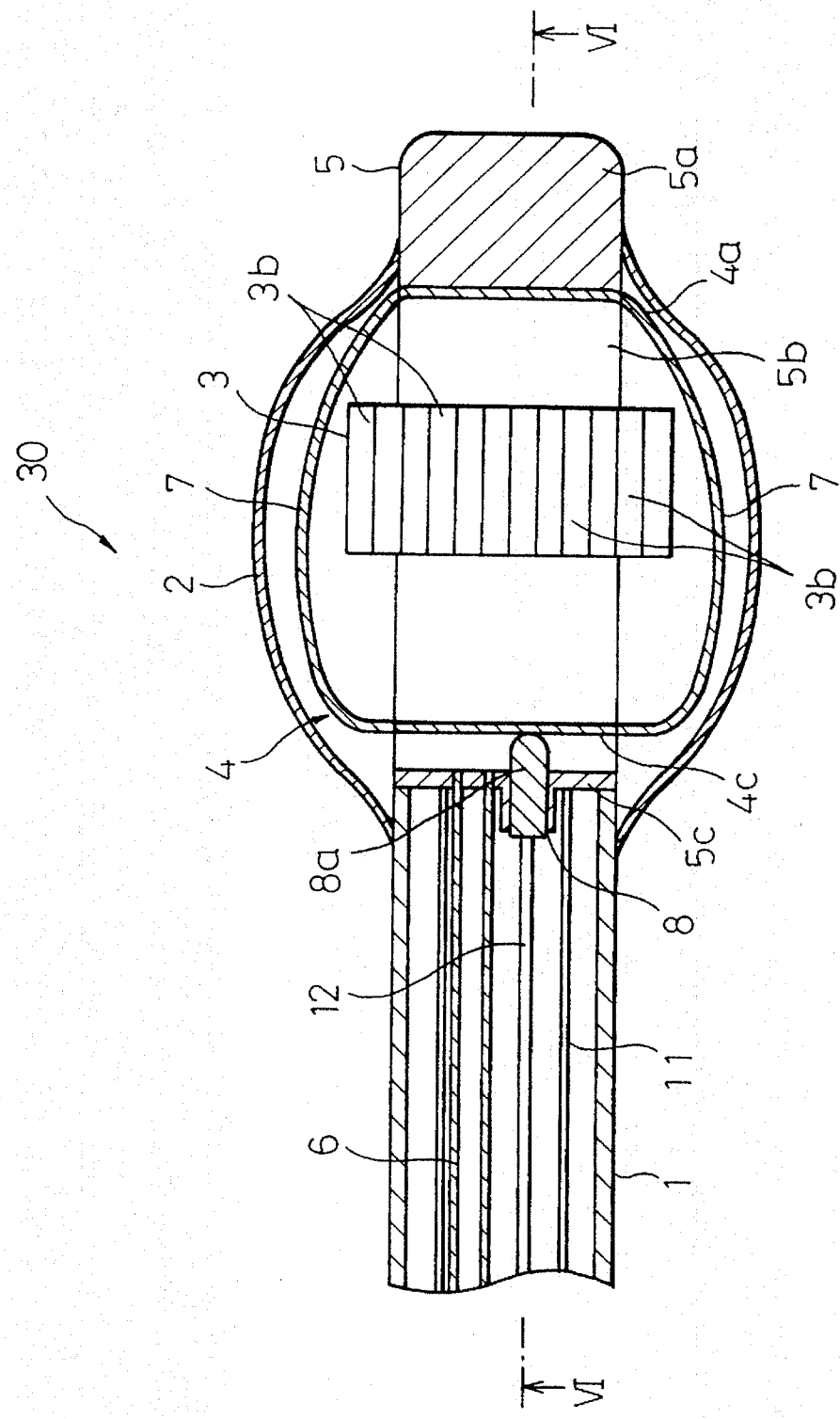
FIG. 5 is a cross-sectional view of the ultrasonic diagnosis of FIG. 3 in another condition.
Figure 6:
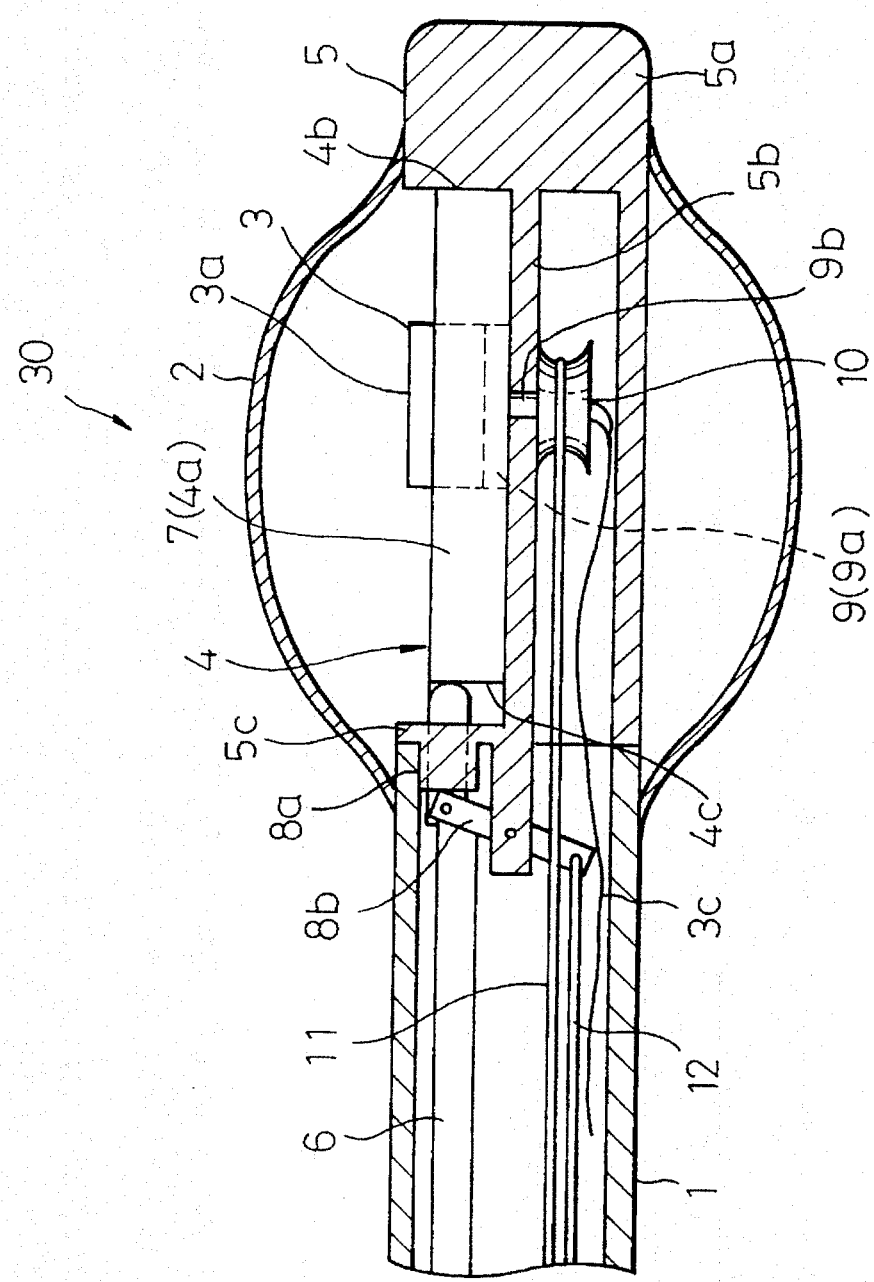
FIG. 6 is a cross-sectional view of the ultrasonic diagnosis of FIG. 5 taken along the line VI—VI in FIG. 5.
Figure 7:
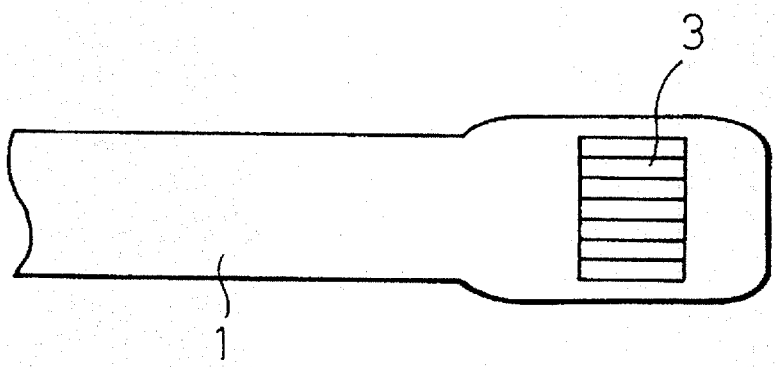
FIG. 7 is a view illustrating a prior art.
Figure 8:
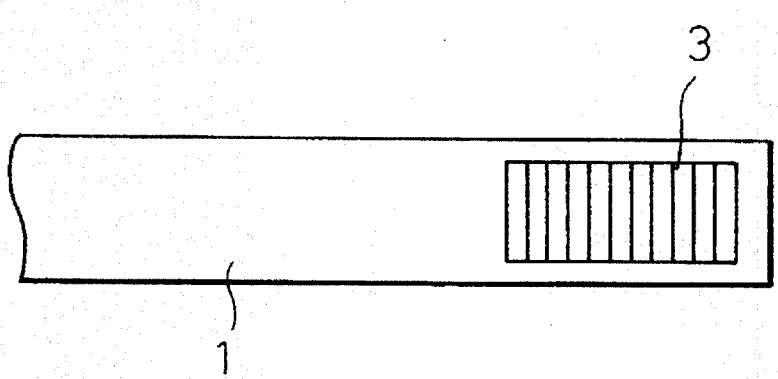
FIG. 8 is a view illustrating a further prior art.
Figure 9:
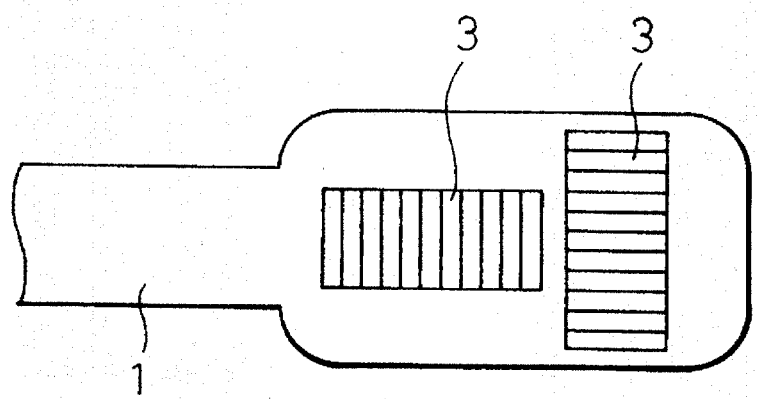
FIG. 9 is a view illustrating a further prior art.
Figure 10:
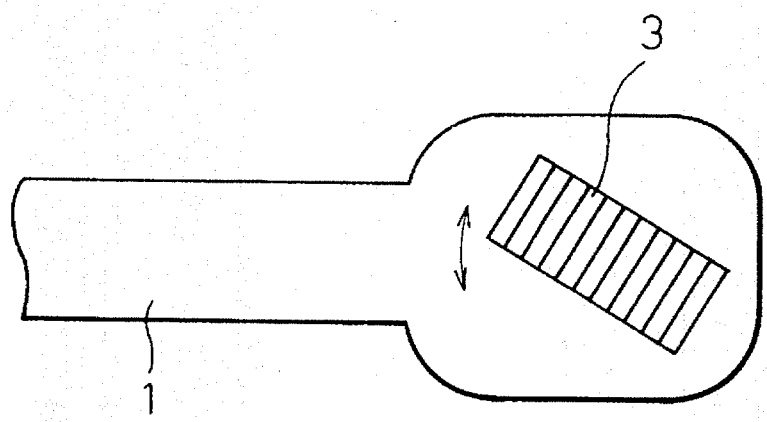
FIG. 10 is a view illustrating a further prior art.

The space ensuring means 4 comprises an elastically deformable annular member 4a and an actuator 8 arranged on the rear side of the annular member 4a. The annular member 4a has a generally rectangular shape and comprises wings (side walls) 7 arranged between the balloon member 2 and the array 3 of piezoelectric elements on either side of the axis of rotation of the latter, respectively, a front wall 4b, and a rear wall 4c. The front wall 4b is arranged in abutment with the rear surface of the head 5a of the cap member 5. The rear wall 4c is arranged in abutment with the an actuator pin 8a of the actuator 8. The wings 7 can be outwardly curved or deformed to open a space delimited by the wings 7 when the actuator pin 8a pushes the rear wall 4c, as shown in FIGS. 5 and 6. The wings 7 are preferably slightly outwardly curved in its initial shape to facilitate the outward deformation thereof.

The actuator 8 comprises the actuator pin 8a slidably inserted in a guide hole in the pin guide wall 5c of the cap member 5, and a lever 8b pivotably carried by the rear end of the support body 5b. The actuator pin 8a is pivotably connected to one end of the actuator pin 8a. A pull wire 12 is connected to the other end of the actuator pin 8a and extends within the tubular support member 1 to a manipulation device (not shown) for operation by an operator.

Therefore, in this embodiment, when the pull wire 12 is pulled by the manipulation device, the actuator pin 8a pushes the rear wall 4c of the annular member 4a to cause the wings 7 to be forcibly outwardly deformed, as shown in FIGS. 5 and 6. The traveling stroke of the actuator pin 8a determined by the pull wire 12 is selected such that a sufficient space is ensured around the array 3 of piezoelectric elements by the outward deformation of the wings 7 so that the array 3 of piezoelectric elements can rotate in said space at the angle of 90 degrees from the position of FIGS. 3 and 4 to the position of FIGS. 5 and 6.

The balloon member 2 is a cylindrical member made of an inflatable material such as rubber. One of the lips of the balloon member 2 is secured to the outer peripheral surface of the end portion of the tubular support member 1, and the other lip is secured to the outer peripheral surface of the head 5a of the cap member 5a, whereby the front opening of the tubular support member 1 is closed. To maintain the ultrasound propagation efficiency, a tube 6 is arranged in the tubular support member 1 for communication with the balloon member 2 to fill the balloon member 2 with a liquid such as water. The balloon member 2 can be inflated by increasing the supply of the liquid.

Figure 3:
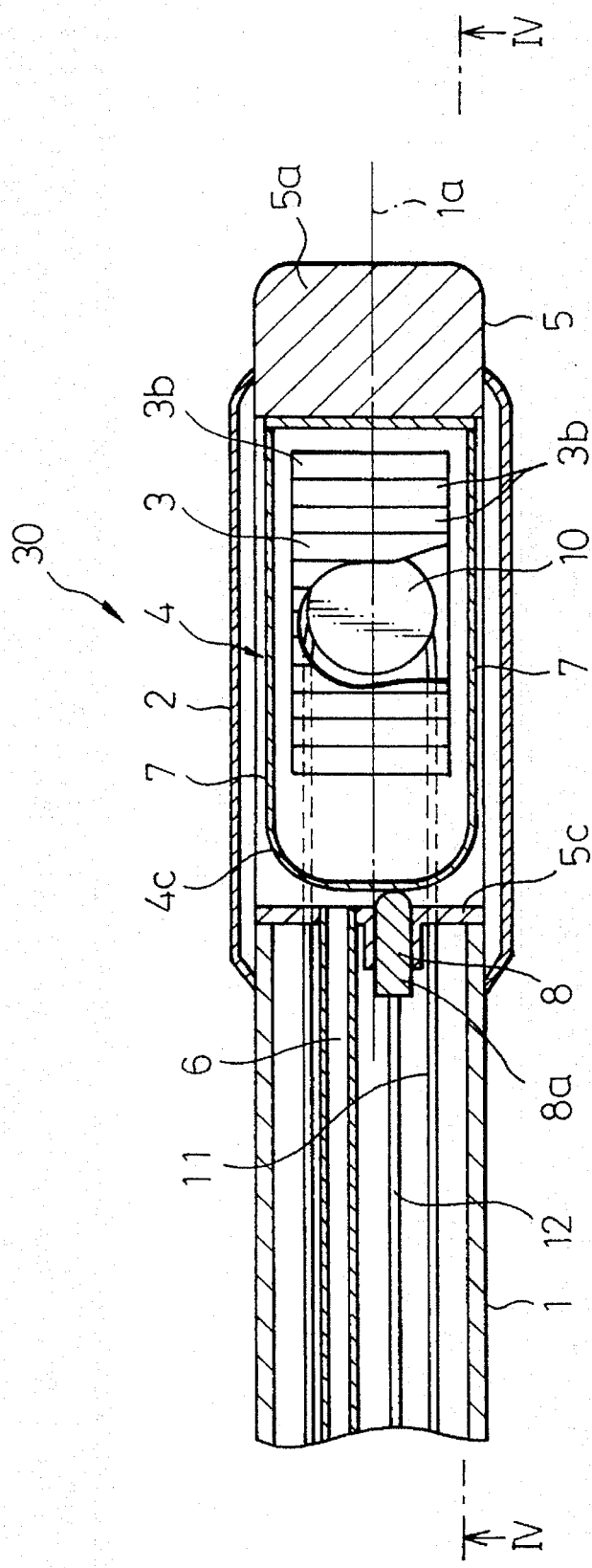
FIG. 3 is a cross-sectional view of an ultrasonic diagnosis probe according to the second embodiment of the present invention.
Figure 4:
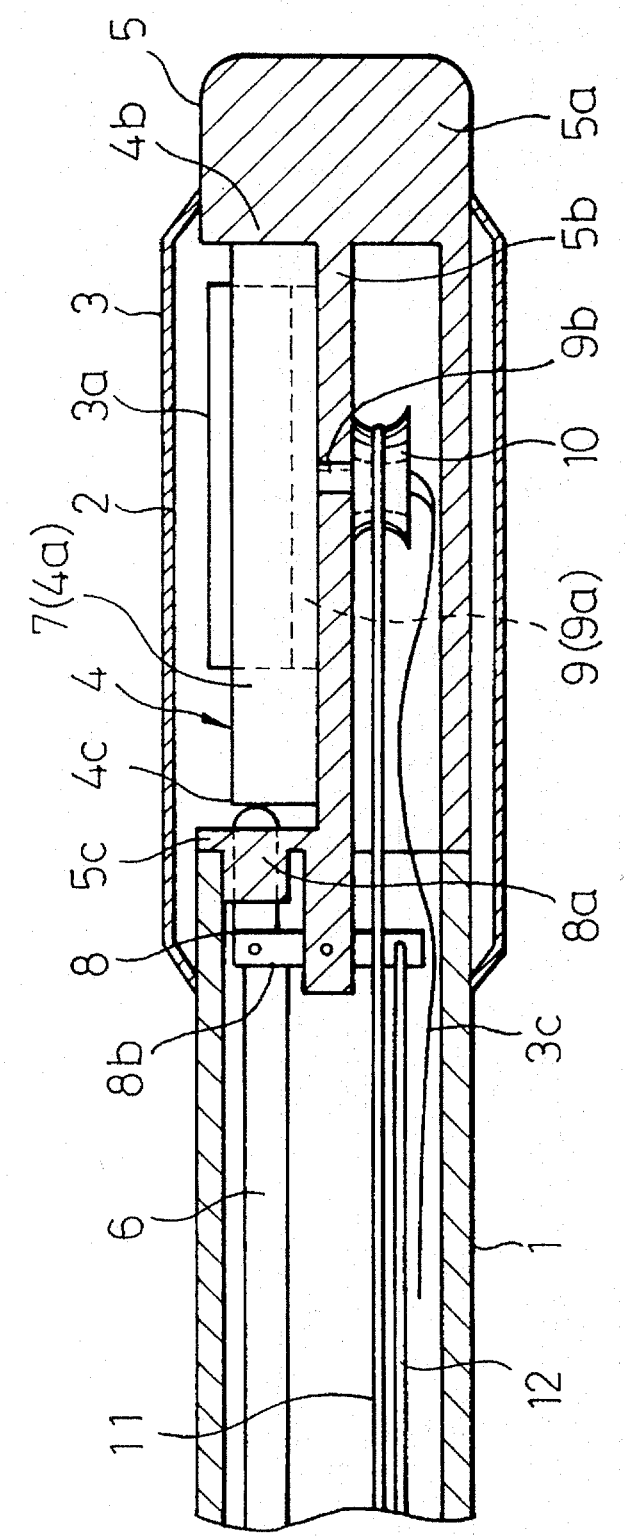
FIG. 4 is a cross-sectional view of the ultrasonic diagnosis of FIG. 3 taken along the line IV—IV in FIG. 3.

The balloon member 2 can be in a deflated condition, as shown in FIGS. 3 and 4. In this condition, each of the wings 7 is arranged between the array 3 of piezoelectric elements 5 and the balloon member 5 generally parallel to the long side of the array 3 of piezoelectric elements which is generally parallel to the axis 1a of the tubular support member 1. The balloon member 2 can also be in an inflated position, as shown in FIGS. 5 and 6. In this position, each of the wings 7 is outwardly curved to open the space for the array 3 of piezoelectric elements, and the array 3 of piezoelectric elements 7 can thus be rotated so that the long sides thereof are generally perpendicular to the axis 1a of the tubular support member 1.

In operation of the ultrasonic diagnosis probe 30, when a diagnosis of a patient is to be carried out, the array 3 of piezoelectric elements is rotated so that the long sides of the latter is generally parallel to the axis 1a of the tubular support member 1. The free end portion of the ultrasonic diagnosis probe 30 has thus a generally uniform tubular shape, and can be smoothly inserted into the esophagus of the patient.

The ultrasonic diagnosis probe 30 may thus reach a desired part of the patient, and an image can be obtained in a plane parallel to the scanning direction. To obtain a further image in a further plane perpendicular to the first plane, the array 3 of piezoelectric elements is rotated by 90 degrees (FIGS. 5 and 6) by operating the wire 11. Prior to the rotation of the array 3 of piezoelectric elements, the wings 7 are forcibly outwardly deformed by operating the pull wire 12 so as to ensure a space in which the array 3 of piezoelectric elements can rotate. When the array 3 of piezoelectric elements is rotated, the liquid is supplied to the balloon member 2 via the tube 6 to increase the volume of the balloon member 2.

The extent of the inflation of the balloon member 2 is determined such that there is no interference between the balloon member 2 and the wall means 4, and in particular, such that the balloon member 2 contacts the wall of the esophagus to provide a clearer image.

In this embodiment, the wall means 4 is provided in the balloon member 2 in order to ensure a space in which the array 3 of piezoelectric elements can rotate. It is, however, possible to omit the space ensuring means 4, and in this case, the balloon member 2 is forcibly inflated by the pressure of the liquid supplied through the tube 6 to ensure a space in which the array 3 of piezoelectric elements can rotate. In the latter arrangement, it is possible to avoid the risk of damaging the balloon member due to an interference between the balloon member 2 and the wall means 4.

In the above described embodiment, the array 3 of piezoelectric elements is rotated by 90 degrees. However, the present invention can be modified so that the array 3 of piezoelectric elements can be rotated to any desired angle. In addition, the array 3 of piezoelectric elements is rotated about an axis of rotation extending perpendicular to the ultrasonic transmitting and receiving surface 3a. However, the present invention can be modified so that an axis of rotation can be arranged in a plane parallel to the ultrasonic transmitting and receiving surface 3a and perpendicular to the long sides of the array 3 of piezoelectric elements.

As explained, it is possible to obtain a high resolution diagnostic image without inflicting pain on a patient.

We claim:

1. An ultrasonic diagnostic probe comprising:

a tubular support member having a free end and an axis;

an inflatable balloon member attached to the free end of the tubular support member;

an array of elongated piezoelectric elements arranged in the balloon member, the array of piezoelectric elements being arranged in a generally rectangular shape with long sides and short sides and rotatable about an axis of rotation; and space ensuring means including a wall means, arranged in the balloon member between the balloon member and the array of piezoelectric elements for ensuring a space in which the array of piezoelectric elements can rotate irrespective of the shape of the balloon member, so that an angle of the long sides of the array of piezoelectric elements relative to the axis of the tubular support member at the free end thereof can be changed.

2. An ultrasonic diagnostic probe according to claim 1, wherein the array of piezoelectric elements has an ultrasonic transmitting and receiving surface and is rotatable about an axis of rotation extending perpendicular to the ultrasonic transmitting and receiving surface.

3. An ultrasonic diagnostic probe according to claim 1, further comprising a cap member fixed to the free end of the tubular support member, the balloon member having a first end attached to the free end of the tubular support member and a second end attached to the cap member, the cap member supporting the array of piezoelectric elements and the space ensuring means.

4. An ultrasonic diagnostic probe according to claim 3, wherein the cap member comprises a body fixed to the free end of the tubular support member and a head located at the distal end of the body, the array of piezoelectric elements being rotatably supported by the body, the second end of the balloon member being attached to the head.

5. An ultrasonic diagnostic probe according to claim 1, further comprising a tube arranged in the tubular support member for introducing fluid into the balloon member to inflate the balloon member.

6. An ultrasonic diagnostic probe according to claim 1, wherein the space ensuring means comprises elastically deformable side walls arranged between the balloon member and the array of piezoelectric elements on either side of the axis of rotation of the array of piezoelectric elements, and an actuator causing the side walls to be deformed to increase or decrease the area delimited by the side walls.

7. An ultrasonic diagnostic probe according to claim 6, wherein the side walls are connected by a rear wall, and the actuator acts on the rear wall to cause the side walls to be deformed.

8. An ultrasonic diagnostic probe according to claim 1, wherein the length of the short sides of the array of piezoelectric elements is approximately identical to or smaller than the diameter of the tubular support member.

9. An ultrasonic diagnostic probe according to claim 1, wherein the balloon member is brought into a slim position when the long sides of the array of piezoelectric elements is generally parallel to the axis of the tubular support member, and into an inflated position when the long sides of the array of piezoelectric elements is at an angle relative to the axis of the tubular support member.

10. An ultrasonic diagnostic probe according to claim 9, wherein the space ensuring means comprises elastically deformable side walls arranged between the balloon member and the array of piezoelectric elements on either side of the axis of rotation of the array of piezoelectric elements, the side walls being arranged generally parallel to the long sides of the array of piezoelectric elements when the balloon member is in the deflated condition, the side walls being outwardly curved relative to the generally parallel position when the balloon member is in the inflated condition.

11. An ultrasonic diagnostic probe comprising:

a tubular support member having a free end and an axis;

an inflatable balloon member arranged on the free end of the tubular support member;

an array of elongated piezoelectric elements arranged in the balloon member, the array of piezoelectric elements having a generally rectangular shape with long sides and short sides and rotatable about an axis of rotation: and a tube arranged in the tubular support member for introducing fluid into the balloon member to inflate the latter, whereby the angle of the long sides of the array of piezoelectric elements relative to the axis of the tubular support member at the free end thereof can be changed.

* * * * *

UNITED STATES PATENT AND TRADEMARK OFFICE
CERTIFICATE OF CORRECTION

PATENT NO. : 5,513,639

DATED : May 7, 1996

INVENTOR(S) : SATOMI et al.

It is certified that error appears in the above-indentified patent and that said Letters Patent is hereby corrected as shown below:

TITLE PAGE: [56] References Cited, under "U.S. PATENT DOCUMENTS", second column, change "5,331,997" to --5,331,947--.

Signed and Sealed this

Twentieth Day of August, 1996

Attest:

BRUCE LEHMAN

*Attesting Officer*　　　　*Commissioner of Patents and Trademarks*